United States Patent [19]

Brown et al.

[11] 4,148,806

[45] Apr. 10, 1979

[54] PROCESS FOR THE PREPARATION OF INDOLOPYRONES

[75] Inventors: Richard E. Brown, Hanover; Paul C. Unangst, Hackettstown; Frank Fontsere, Andover; Arthur C. Fabian, Flanders, all of N.J.

[73] Assignee: Warner-Lambert Company, Morris Plains, N.J.

[21] Appl. No.: 860,504

[22] Filed: Dec. 14, 1977

Related U.S. Application Data

[62] Division of Ser. No. 764,110, Jan. 31, 1977, abandoned.

[51] Int. Cl.$^2$ .............................................. C07D 491/04
[52] U.S. Cl. .............................. 260/326.29; 260/326.16

[58] Field of Search ..................................... 260/326.29

[56] References Cited

U.S. PATENT DOCUMENTS

| 3,868,387 | 2/1975 | Berger et al. | 260/326.29 |
| 4,028,383 | 6/1977 | Brown et al. | 260/326.29 |
| 4,056,536 | 11/1977 | Atkinson et al. | 260/326.29 |

*Primary Examiner*—Donald G. Daus
*Assistant Examiner*—David E. Wheeler
*Attorney, Agent, or Firm*—Albert H. Graddis; Frank S. Chow

[57] ABSTRACT

This invention relates to a novel process for preparing a group of novel substituted indolopyrones.

1 Claim, No Drawings

PROCESS FOR THE PREPARATION OF INDOLOPYRONES

This is a division, of application Ser. No. 764,110 filed Jan. 31, 1977, now abandoned.

This invention relates to substituted indolopyrones of the general formula:

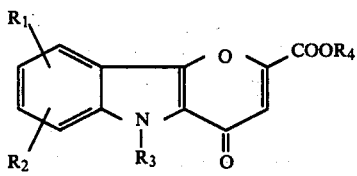

wherein $R_1$ and $R_2$ may be hydrogen, halogen, or lower alkyl of 1 to 6 carbon atoms; $R_3$ may be lower alkyl of 1 to 6 carbon atoms, benzyl or phenyl and $R_4$ may be hydrogen or lower alkyl of 1 to 6 carbon atoms in length.

The compounds of this invention are prepared in a manner similar to that of U.S. patent application Ser. No. 611,453, which is now U.S. Letters Patent No. 4,028,383, the disclosure of which is incorporated in toto with the exception that the intermediate ketone II is prepared by reacting a substituted anthranilic acid of structure I with chloroacetone in the presence of a base.

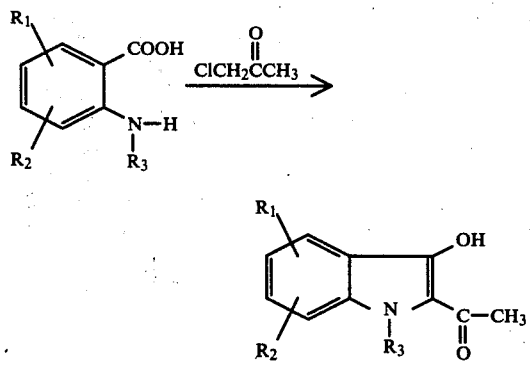

In structures I and II, $R_1$ and $R_2$ may be hydrogen, hydroxy, lower alkoxy or lower alkyl of 1 to 6 carbon atoms, halogen, trifluoromethyl, or may be taken together to form a methylenedioxy group. $R_3$ may be hydrogen, lower alkyl of 1 to 6 carbon atoms, phenyl, or a phenylalkylene group of 1 to 6 carbons in the chain. Preferably, however, $R_1$, $R_2$ and $R_3$ are as defined for the indolopyrone of this invention.

The reaction of the substituted anthranilic acid with chloroacetone is best carried out in a hydroxylic solvent such as water, lower molecular weight alcohol, or an aqueous alcohol solution. The base used may be alkali hydroxide or carbonate such as sodium hydroxide, sodium bicarbonate, or, preferably, potassium carbonate.

The intermediate ketone is then reacted with a lower alkyl ester of oxalic acid in the presence of a strong base to give the indolopyrone according to this invention in which $R_1$, $R_2$, $R_3$ are as defined and $R_4$ is lower alkyl of 1 to 6 carbon atoms. Among the strong bases which may be used for this reaction are sodium hydride, sodium amide, potassium t-butoxide, or, preferably, sodium ethoxide. The reaction is conveniently carried out in a solvent such as ethanol, THF, DMF, DMSO, and the like.

In the final step, saponification of the ester of the indolopyrone wherein $R_4$ is a lower alkyl group is carried out to afford the acid of the indolopyrone wherein $R_4$ is hydrogen.

The following examples are given in order to more fully disclose the process according to our invention as used to prepare the pharmaceutically active series of indolopyrones having antiallergic activity.

EXAMPLE 1

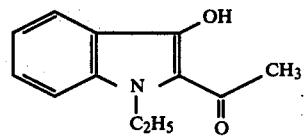

1-Ethyl-3-hydroxy-1H-indol-2-yl methyl ketone. A mixture of 35.0 g (0.212 mole) 2-ethylaminobenzoic acid, 30.0 g (0.217 mole) potassium carbonate, and 42.9 g (0.465 mole) distilled chloroacetone in 350 ml water and 150 ml ethanol was stirred at reflux for 90 min. The reaction mixture was cooled, stirred in ice for 1 hr, and the crude solid product was filtered and washed with cold water. After suspending the crude solid in 500 ml of 0.5 N aqueous NaOH, the mixture was digested with charcoal for 15 min on the steam bath and then filtered hot. The filtrate was cooled in ice and acidified with 4 N HCl. The green precipitate was filtered, washed with cold water, then digested (steam) briefly in 750 ml 5% aqueous $NaHCO_3$, refiltered and again washed with water. Several recrystallizations from aqueous methanol yielded yellow needles of mpt. 119.5°–121°.

Anal. Calcd. for $C_{12}H_{13}NO_2$: C, 70.91; H, 6.45; N, 6.89; Found: C, 70.70; H, 6.53; N, 6.86.

EXAMPLE 2

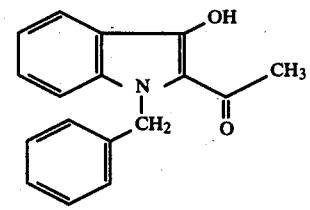

3-Hydroxy-1-phenylmethyl-1H-indol-2-yl methyl ketone. A mixture of 140 g (0.618 mole) 2-(phenylmethylamino)benzoic acid, 43.0 g (0.311 mole) potassium carbonate, and 60 g (0.650 mole) distilled chloroacetone in 900 ml water and 400 ml ethanol was stirred at reflux for 18 hr. The cooled reaction mixture was treated in the manner described in Example 1. Several recrystallizations of the final product from aqueous methanol yielded light green needles of mpt. 149.5°–151.5°.

Anal. Calcd. for $C_{17}H_{15}NO_2$: C, 76.96; H, 5.70; N, 5.28; Found: C, 76.81; H, 5.80; N, 5.27.

EXAMPLE 3

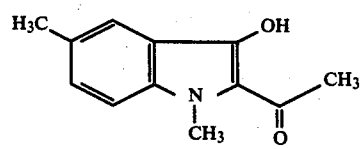

1,5-Dimethyl-3-hydroxy-1H-indol-2-yl methyl ketone. In a manner analogous to that of Example 1, the title compound was prepared from 5-methyl-2-methylaminobenzoic acid. Several recrystallizations of the final product from aqueous methanol yielded yellow flakes of mpt. 120°-122°.

Anal. Calcd. for $C_{12}H_{13}NO_2$: C, 70.91; H, 6.45; N, 6.89; Found: C, 70.87; H, 6.43; N, 7.02.

EXAMPLE 4

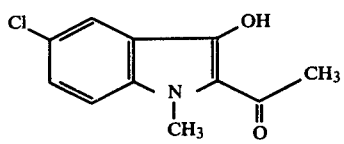

5-Chloro-3-hydroxy-1-methyl-1H-indol-2-yl methyl ketone. In a manner analogous to that of Example 1, the title compound was prepared from 5-chloro-2-methylamino-benzoic acid. Several recrystallizations of the final product from aqueous methanol yielded a green solid of mpt. 177°-dec.

Anal. Calcd. for $C_{11}H_{10}ClNO_2$: C, 59.07; H, 4.51; N, 6.26; Cl, 15.85; Found: C, 58.95; H, 4.59; N, 6.09; Cl, 15.75.

EXAMPLE 5

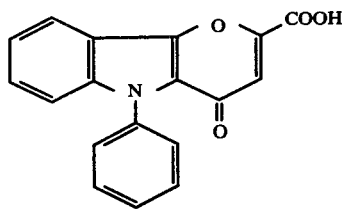

4,5-Dihydro-4-oxo-5-phenylpyrano[3,2-b]indole-2-carboxylic acid. A mixture of 1.0 g (0.0033 mole) of ethyl 4,5-dihydro-4-oxo-5-phenylpyrano [3,2-b]indole-2-carboxylate in 10 ml glacial acetic acid and 2.0 ml conc. hydrochloric acid was stirred at reflux for 4½ hr, then cooled and added to 75 g ice - $H_2O$. The solid was filtered, washed with cold water, then added to a mixture of 35 ml 5% aqueous sodium carbonate and 250 ml water. After filtering by gravity, tha aqueous solution was washed three times with 75 ml chloroform, cooled in ice, and acidified with 4.0 N hydrochloric acid. The orange precipitate was filtered, digested 15 min on the steam bath with 25 ml water and re-filtered warm. Recrystallization from DMF-water yielded an off-white solid of mpt.>290°.

Anal. Calcd. for $C_{18}H_{11}NO_4$: C, 70.81; H, 3.63; N, 4.59; Found: C, 70.77; H, 3.69; N, 4.49.

EXAMPLE 6

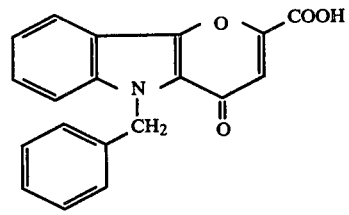

4,5-Dihydro-4-oxo-5(phenylmethyl)pyrano[3,2-b]indole-2-carboxylic acid. A mixture of 6.0 g (0.017 mole) of ethyl 4,5-dihydro-4-oxo-5-(phenylmethyl)pyrano[3,2-b]indole-2-carboxylate, 80 ml 1% aqueous sodium hydroxide, and 450 ml water was stirred at room temperature for 3 hr. Ethanol (~150 ml) was then added until virtually all of the insoluble material present had dissolved. After washing twice with 250 ml of chloroform, the aqueous layer was filtered by gravity, cooled in ice, and acidified with 4 N hydrochloric acid. The tan precipitate was filtered, digested for 15 min on the steam bath with 100 ml of water and re-filtered while still warm. Recrystallization of the final product from DMF-water yielded a white powder of mpt. 290°-dec.

Anal. Calcd, for $C_{19}H_{13}NO_4$: C, 71.47; H, 4.10; N, 4.39; Found: C, 71.21; H, 4.24; N, 4.38.

EXAMPLE 7

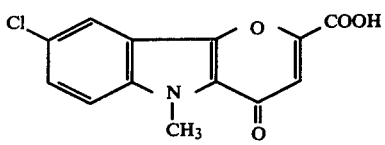

8-Chloro-4,5-dihydro-5-methyl-4-oxopyrano[3,2-b]indole-2-carboxylic acid. A mixture of 3.5 g (0.012 mole) of ethyl 8-chloro-4,5-dihydro-5-methyl-4-oxopyrano[3,2-b]indole-2-carboxylate in 50 ml glacial acetic acid and 10 ml conc. hydrochloric acid was stirred at reflux for 3 hr, then cooled and added to 500 g ice - $H_2O$. The crude product was filtered, washed with 50% aqueous ethanol, and air dried. A suspension of the product in 75 ml of chloroform was stirred for 90 min at room temperature, then filtered. After recrystallization twice from DMF-water, the final product was dried for several hours under high vacuum at 100°. The yellow flakes obtained had a mpt. of 290°-dec.

Anal. Calcd. for $C_{13}H_8ClNO_4$: C, 56.24; H, 2.90; N, 5.05; Cl, 12.77; Found: C, 56.10; H, 3.14; N, 5.01; Cl, 13.04.

The compounds of this invention are useful in the prevention of allergic and asthmatic reactions in mammals. For examples in tests conducted by the procedures of I. Mota and Z. Ovary, these compounds were capable of protecting rats from allergic and asthmatic reactions at a dose level of 0.5 to 5 mg/kg when administered perenterally and at a dose level of 0.1 to 1.0 mg/kg when administered intravenously. The passive cutaneous anaphylaxis procedure also showed these compounds to be antiallergic.

We claim:

1. A process for preparing a compound of the formula:

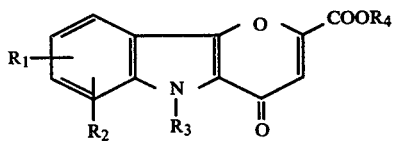

wherein $R_1$ and $R_2$ may be hydrogen, hydroxy, lower alkoxy or lower alkyl of 1–6 carbon atoms, halogen, trifluoromethyl, or, taken together, methylenedioxy; $R_3$ may be hydrogen, lower alkyl of 1–6 carbon atoms, phenyl methyl or phenyl; and $R_4$ may be hydrogen or lower alkyl of 1-6 carbon atoms, comprising the steps of:

A. Reacting a substituted anthranilic acid of the formula:

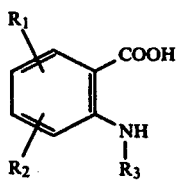

with chloracetone in the presence of a base and a hydroxylic solvent to obtain a compound of the structure:

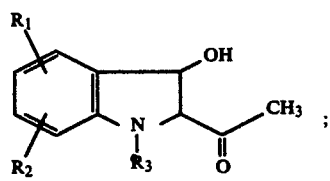

B. Reacting the compound so obtained with a lower alkyl ester of oxalic acid in the presence of a strong base to obtain a compound of the structure:

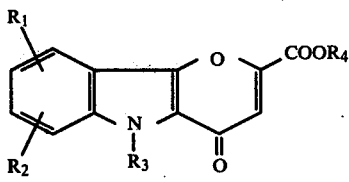

wherein $R_4$ is a lower alkyl of 1-6 carbon atoms; and

C. Reacting the ester so obtained with aqueous strong base followed by strong acid or with aqueous strong acid alone to obtain the desired compound:

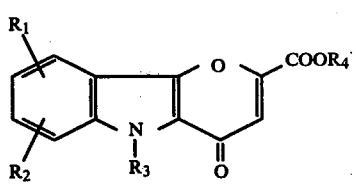

wherein $R_4$ is hydrogen.

* * * * *